United States Patent [19]

Jolly

[11] Patent Number: Plant 5,835

[45] Date of Patent: Dec. 23, 1986

[54] ROSE PLANT

[75] Inventor: Nelson F. Jolly, Galena, Md.

[73] Assignee: Jolly's Rosehill Farm of Kent, Inc., Galena, Md.

[21] Appl. No.: 702,376

[22] Filed: Feb. 15, 1985

[51] Int. Cl.[4] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new miniature rose variety of carrot red to Spanish orange coloring.

1 Drawing Figure

The present invention relates to a new and distinct variety of rose plant of the miniature rose class, which was originated by my crossing as seed parent the rose known as "Rise N' Shine" and as pollen parent the rose known as "First Prize". The varietal denomination of this new variety is "Nelo".

Among the novel characteristics possessed by this new variety which distinguish it from its parents and all other varieties of which I am aware are its attractive bud form and flower coloring in the range of carrot red to Spanish orange which maintains its color and form. Flowers are long lasting on the plant and as cut flowers. Asexual reproduction by budding of the new variety as performed in Kent County, Md., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "29A" is plate 29A of The Royal Horticultural Society Colour Chart.

Parentage: Seedling.

*Seed parent.*—Rise N' Shine".

*Pollen parent.*—"First Prize".

Class: Miniature.

The following observations are made of specimens grown under glass, in Kent County, Md., during the month of July.

FLOWER

Blooming habit: Near continuous.

A. Bud:

(1) *Size.*—Medium to small.

(2) *Form.*—Pointed, ovate.

(3) *Color.*—When sepals first divide — near carrot red 29A. When petals begin to unfurl — bud color lightens to shades of 26D, Spanish orange, and 27C.

(4) *Sepals.*—As long as bud, near 138A.

(5) *Peduncle.*—Length — about ¾ to 1 inch. Aspect — straight. Strength — erect. Color — near 145A.

B. Bloom:

(1) *Size.*—Average size when fully expanded — about 1½ to 2 inches.

(2) *Borne.*—Singly.

(3) *Form.*—High centered, exhibition form to about ⅓ open, outer petals reflex upon opening.

(4) Petalage.—Number of petals under normal conditions — about 20 to 25.

(5) *Color.*—Attractive, well formed buds beginning as carrot red 29A, lighten as petals unfurl to shades of Spanish orange 26D. As flowers open further, predominant coloring remains Spanish orange 26C and 26D. Tonality of flower centers appears deeper where petals bunch (near 29B).

C. Petals:

(1) *Texture.*—Medium.

(2) *Appearance.*—Inside — velvety, outside — velvety.

(3) *Form.*—Broad, fan shaped with pronounced apex on many petals.

(4) *Arrangement.*—Regularly arranged, shingle-like.

(5) *Petaloids in center.*—Few.

(6).Persistence.—Drop off cleanly.

(7) *Fragrance.*—Slight.

(8) *Lasting quality.*—Long lasting on plant (up to 7 days) and long lasting as cut flower (up to 5 days).

REPRODUCTIVE ORGANS

A. Stamens, filaments and anthers:

(1) *Arrangement.*—Regularly arranged around styles.

(2) *Color.*—Near 25A.

B. Pollen:

*Color.*—Near 25A.

C. Styles: Even length, bunched.

D. Stigmas:

*Color.*—Near 22B.

E. Hips: Globular, ½ to ¾ inch, yellow orange, seeds do not protrude.

PLANT

A. Form: Spreading.

B. Growth: Very vigorous, uniform branching.

*Height attained.*—about 6 to 12 inches.

C. Foliage: Compound 5 to 7 leaflets.

(1) *Size.*—Small to medium.
(2) *Quantity.*—Abundant.
(3) *Color.*—New foliage: Upper side — near to 139C. Under side — near to 139C. Old foliage: Upper side — near 139A. Under side — near 139C.
(4) *Shape.*—Oval.
(5) *Texture.*—Upper side is waxy and under side is matte.
(6) *Edge.*—Serrated.
(7) *Serration.*—Serrulate.
(8) *Leaf stem.*—Color — near 139B. Under side — near 139B.
(9) *Stipules.*—Slightly bearded.
(10) *Resistance to disease.*—Blackspot — average. Mildew — average. Rust — not observed.

D. Wood:
(1) *New wood.*—Color — near 141C. Bark — smooth.

(2) *Old wood.*—Color — near 138A. Bark — smooth.

E. Thorns:
(1) *Thorns.*—Quantity (main stalk): ordinary. On laterals from stalk — few Form — straight, flat base. Size — small. Color — near 144D. Position — irregular.
(2) *Prickles.*—None.

F. Winter hardiness: Requires ordinary protection in extreme climates.

I claim:

1. A new and distinct variety of rose plant of the miniature rose class, substantially as shown and described, characterized particularly by attractive well-formed buds and flowers of the carrot red to Spanish orange color class displayed on a relatively low growing plant with abundant dark green foliage.

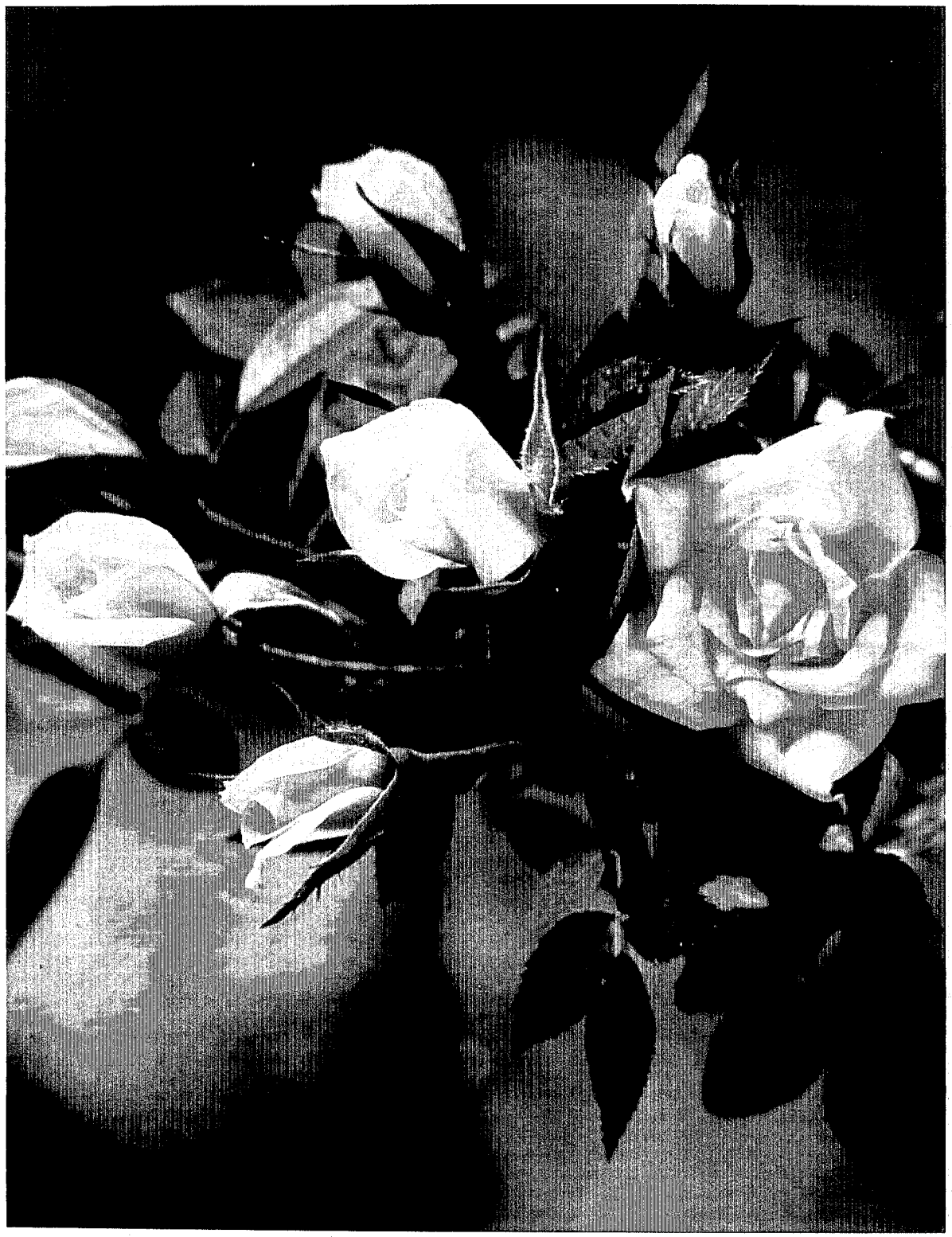

* * * * *